(12) United States Patent
Iwasaki et al.

(10) Patent No.: US 7,002,150 B2
(45) Date of Patent: Feb. 21, 2006

(54) THIN SPECIMEN PRODUCING METHOD AND APPARATUS

(75) Inventors: Kouji Iwasaki, Chiba (JP); Yutaka Ikku, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 10/854,868

(22) Filed: May 27, 2004

(65) Prior Publication Data

US 2004/0245464 A1 Dec. 9, 2004

(51) Int. Cl.
*G21K 7/00* (2006.01)
(52) U.S. Cl. .................................. 250/307; 250/492.21
(58) Field of Classification Search ........... 250/492.21, 250/307, 310
See application file for complete search history.

(56) References Cited

U.S. PATENT DOCUMENTS 6,664,552 B1 * 12/2003 Shichi et al. .......... 250/492.21

* cited by examiner

*Primary Examiner*—Kiet T. Nguyen
(74) *Attorney, Agent, or Firm*—Adams & Wilks

(57) ABSTRACT

A thin specimen producing method acquires a work amount in a 1-line scan by an FIB under a predetermined condition, measures a remaining work width of a thin film on an upper surface of a specimen by a microscopic length-measuring function, determines a required number of scan lines of work to reach a predetermined width by calculation, and executes a work to obtain a set thickness. The work amount in a one-line scan by the FIB under the predetermined condition is determined by working the specimen in scans of plural lines, measuring the etched dimension by the microscopic length-measuring function, and calculating an average work amount per one-line scan.

7 Claims, 5 Drawing Sheets

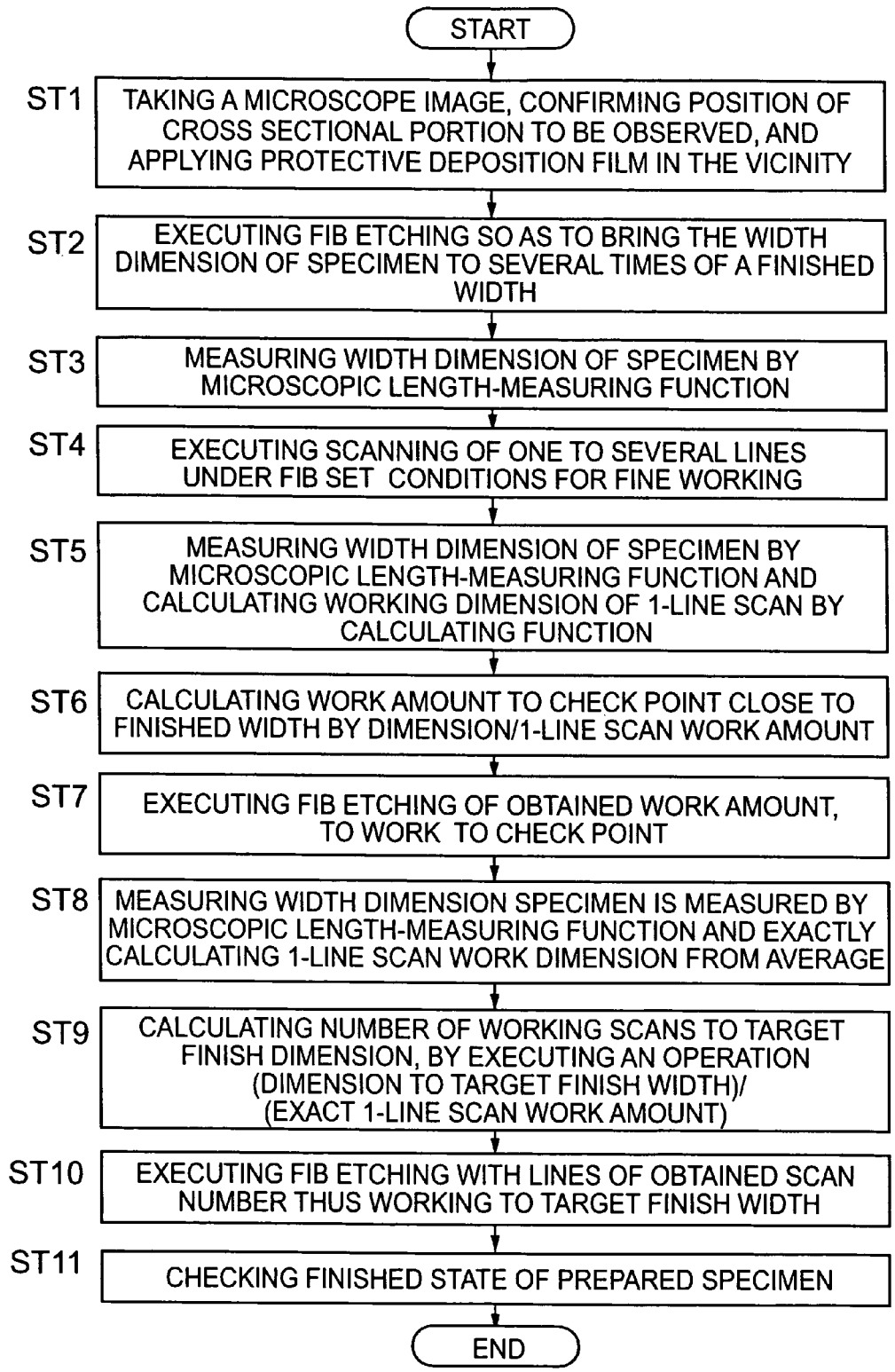

MOUNTING OF SPECIMEN PIECE TO FIXING SUPPORT

TEM SPECIMEN FINISH WORKING

THIN SPECIMEN PRODUCING METHOD AND APPARATUS

BACKGROUND OF THE INVENTION

The present invention relates to a technology of forming a specimen of a transmission electron microscope (TEM specimen) into a thin specimen by a focused ion beam.

It is already known to prepare a thin specimen, for a cross-sectional observation by a transmission electron microscope (TEM), by a thin film working with a focused ion beam (FIB) apparatus, and there are known (1) a method of executing an etching work in a wafer state thereby obtaining a thin film specimen formed into a thin piece, and (2) a method of mechanically cutting out a small piece from a wafer-shaped specimen and working on such piece.

In the method (1), as shown in FIGS. 4A–4D, a portion desired for cross-sectional observation is specified in a large specimen such as a wafer, then an FIB irradiation is executed under a blowing of a raw material gas from a gas gun to apply a protective deposition film, then holes are formed by an FIB etching on both sides of such cross section, further the cross-sectional portion for observation is worked into a thin piece and then cut in periphery, and the thin specimen is lifted out by a glass probe through an operation of a manipulator (not shown) and is fixed on a mesh of an organic thin film to constitute a TEM specimen.

In case of preparing a cross-sectional TEM specimen by the method (2), at first, on a small-piece specimen shaped into several tens of micrometers by a mechanical polishing as shown in FIG. 5A, an FIB irradiation is executed under a blowing of a raw material gas by a gas gun to apply a protective deposition film in front of and behind a portion to be observed, as shown in FIG. 5B. In this specimen, an FIB etching work is executed to leave a wall of 0.5 $\mu$m or less as shown in FIG. 5C. Then the specimen after the working is observed under a TEM as shown in FIG. 5D to confirm whether the working is done to have an appropriate thickness. In case the working is insufficient, the ion beam etching work has to be executed again. This method, requiring to transfer the specimen between plural vacuum apparatuses, namely the FIB apparatus and the TEM apparatus, is associated with drawbacks of requiring a time for evacuation and positioning of the specimen, and of difficulty in preparing an optimum cross-sectional TEM specimen.

In order to resolve such drawbacks, the present applicant already proposed a "focused ion beam apparatus and a working observing method" in JP-A No. 6-231720. A focused ion beam apparatus for working, disclosed in the patent, is provided as shown in FIG. 6 with an electron lens barrel (electron gun 6, electron optical system 8) in addition to an ion lens barrel (ion gun 1, ion optical system 3), and characterized in including an irradiation system for irradiating the specimen with an electron beam from a lateral direction and detectors 5, 9, 11, 10 for detecting electron beam-excited secondary signals (secondary electrons, reflected electrons, transmitted electrons, Auger electrons and X-ray), and is capable of scanning with the FIB 2 and detecting ion beam-excited secondary electrons to observe an image of a scanning ion microscope (SIM) thereby determining a working observing position of a specimen, and then executing an ion beam etching work on the surface of the worked specimen, thereby achieving a thin piece formation of a specified position of the specimen, particularly preparation of a cross-sectional TEM specimen. It is also possible to switch the ion beam to an aforementioned electron beam whenever necessary thereby observing a working state by a SEM image or monitoring reflected electrons, transmitted electrons, or an X-ray excited by transmitted and scattered electrons, thereby estimating the thickness of the thin specimen. This apparatus enables to work a specified part of the specimen into a thin piece by FIB etching and to switch the ion beam into the electron beam whenever necessary during the working operation without changing the apparatus whereby a SEM image observation or an X-ray analysis can be executed to easily achieve a confirmation of a working position, a working shape or a cross section or an analysis of a small portion, and a monitoring of reflected electrons, transmitted electrons or transmitted and scattered electrons allows to check the thickness of the thin-worked specimen by an electron transmittance thereof instead of a mere confirmation of the dimension, and thus provides an advantage that an appropriate thin film working can be easily executed. In the aforementioned apparatus, however, though the transfer of the specimen between the different apparatus, namely between the FIB apparatus and the electron microscope is unnecessary, it is still necessary, in order to execute the necessary thin film working, to interrupt the working in the course thereof, then to confirm the film thickness by the STEM image observation in the lateral direction, and repeating the working and the confirmation of film thickness, thus requiring works by the operator and a working time.

Under such situation, there is being adopted, in case of working specimens of a same structure in a same material, a method of preparing a working recipe by confirming the working conditions in advance and executing the working thereafter based on such recipe thereby obtaining an approximately required thickness. There is also being developed an apparatus for automatic working by programming such method, and the TEM specimen working that has required a professional skill can now be simply achieved even to an unskilled person by such programmed working. However, the preparation of such working recipe requires a skill as in the past and also requires a working time corresponding to several TEM specimens. Therefore, in case the number of the specimen is limited, the specimen working is being executed in the prior method since the recipe preparation requires more time. Also the method of estimating the film thickness of the specimen in the course of FIB working, utilizing the signal of electrons reflected or transmitted by the thin film or X-ray induced by the electrons, is acceptable for a specimen bearing no pattern and having a similar structure in any position, but, in case of a device having a complex cross-sectional structure such as an LSI, it is still necessary to interrupt the operation in the course of the working, then to confirm the film thickness based on the signal from the cross section and to re-start the working, and to thereafter repeat the interruption of the working and the confirmation of the film thickness, thus necessitating a time for the working.

An object of the present invention is to provide a method capable of achieving a control of a set film thickness by the FIB working without a working recipe for thin film working and enabling a fine working such as of a TEM specimen in a simple manner even with a skill of a certain level, and a system for executing such method.

SUMMARY OF THE INVENTION

A thin specimen producing method of the present invention is to acquire a work amount in a 1-line scan by a FIB under a predetermined condition, also to measure a remaining work width of a thin film on an upper surface of a specimen by a microscopic length-measuring function, to determine a required number of scan lines of work to reach a predetermined width by calculation, and to execute a work to obtain a set thickness. The method for determining the work amount in a 1-line scan by a FIB under the predetermined condition includes working the specimen in scans of plural lines, measuring the etched dimension by the microscopic length-measuring function, and calculating an average working amount per 1-line scan. The microscopic length measurement is achieved by executing a pattern matching, utilizing a SIM image by the working FIB or a monitoring SEM image and based on a drift correcting mark provided on a specimen surface, and measuring a thickness of a finished surface in a designated position of the TEM specimen.

A system of the present invention for executing a fine working such as of a TEM specimen includes means which memorizes a work amount of a line by working with a charged particle beam such as an FIB under a specified condition, means which acquires a microscope image of an upper surface of a specimen thereby automatically measuring a remaining work width of a thin film; means which calculates a required number of scan lines to reach a predetermined width based on the work amount per line, and means which executes a work with the FIB (charged particle beam); wherein an automatic working is executed to obtain a target thickness, under working and under confirmation of a work amount by measuring the remaining work width of the thin film according to a set program. As the length measuring means, there is provided an electron microscope apparatus functioning asynchronously with the FIB, and, as the microscope image, a SEM image or a reflected electron image is used. Also as the means for confirming the working thickness, electron beam irradiating means and means which detects a signal of reflected electrons, transmitted electrons or an electron-induced X-ray and the working thickness is confirmed by the detection of such signal.

BRIEF DESCRIPTION OF THE DRAWINGS

FIG. 2 is a flowchart showing a sequence of a film thickness control method in the thin film working.

DETAILED DESCRIPTION OF THE INVENTION

Figure 3A:
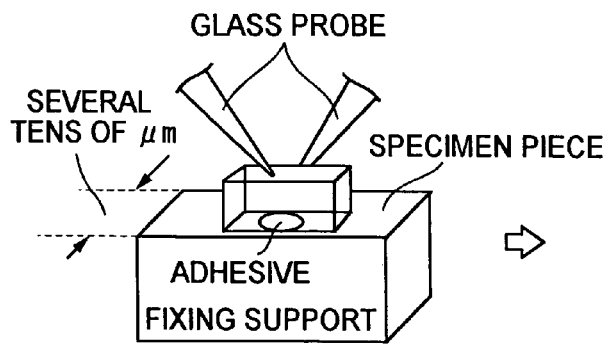
FIGS. 3A–3B are views showing form and working of a lift-out specimen enabling a follow-up working.
Figure 3B:
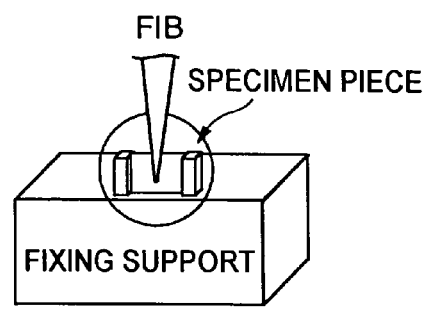
Figure 4A:
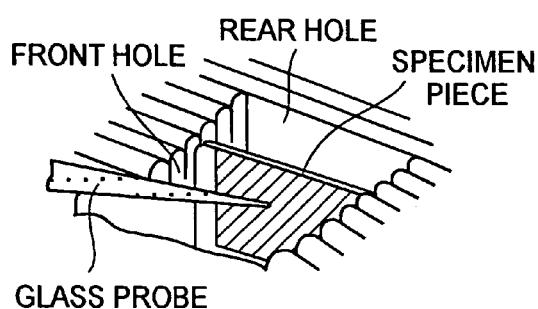
FIGS. 4A–4D are views showing one of the prior TEM specimen producing methods.
Figure 4C:
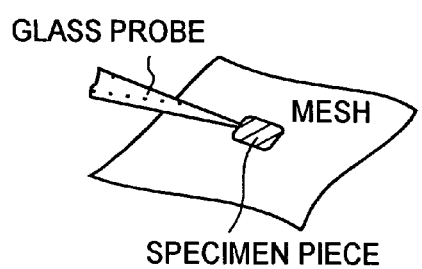
Figure 4B:
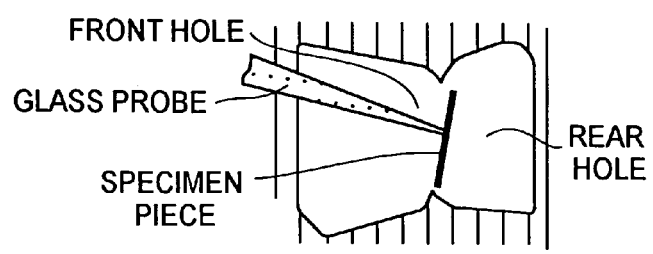
Figure 4D:
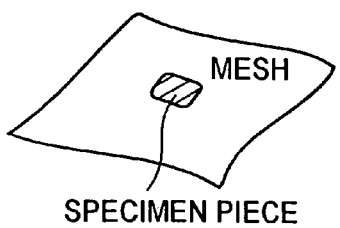
Figure 5A:
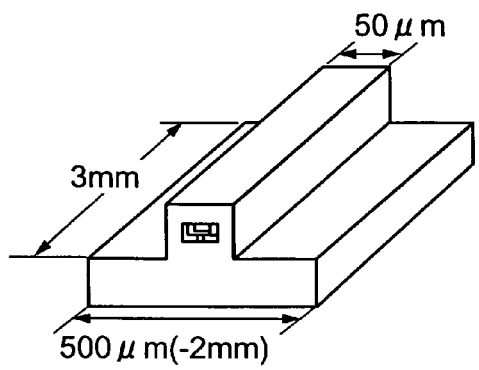
FIGS. 5A–5D are views showing another of the prior TEM specimen producing methods.
Figure 5B:
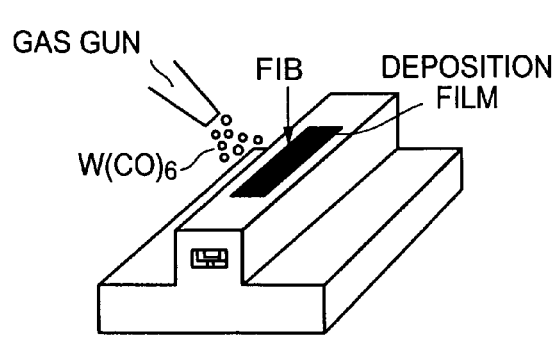
Figure 5C:
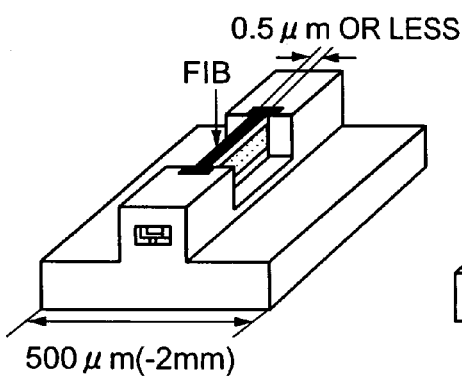
Figure 5D:
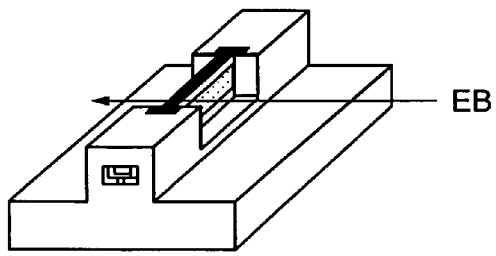
Figure 6:
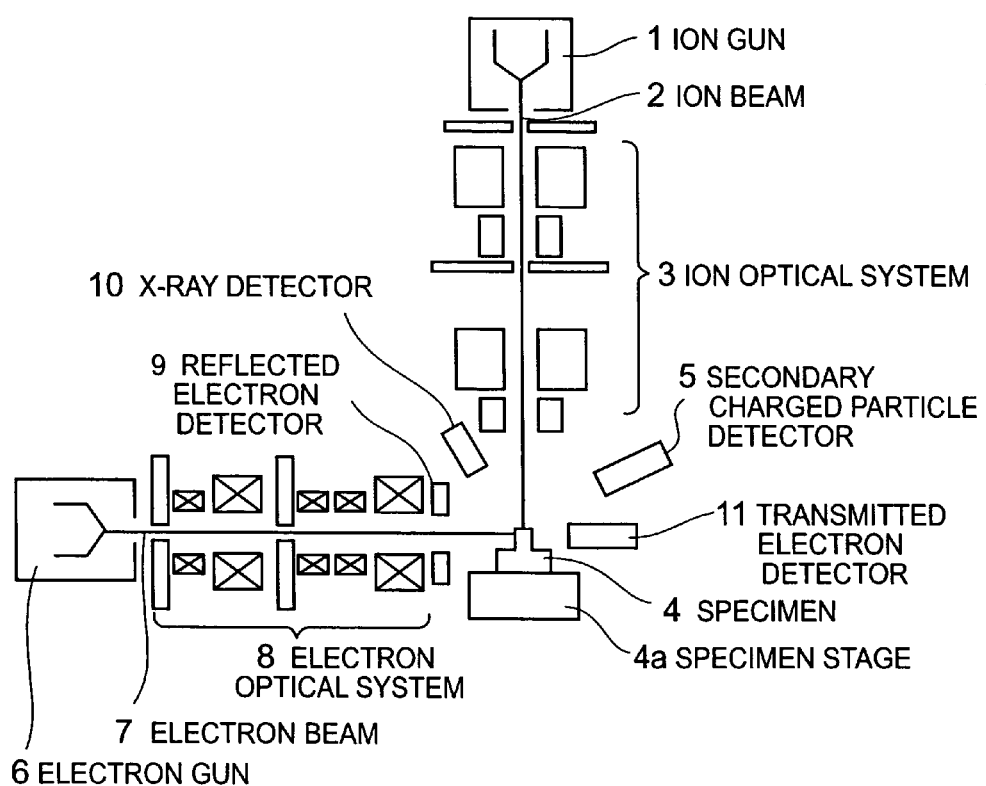
FIG. 6 is a view showing an FIB apparatus for producing a TEM specimen.

The present invention is to provide, in a TEM specimen producing method of mechanically cutting out a small piece from a large specimen and working the same as shown in FIG. 5, a method of enabling easy working even for an unskilled person and in the absence of a working recipe, and a system for executing such method. However, it is applicable also, even in a method of directly etching a large specimen to take out a thin worked specimen, to a specimen of an FIB lift out method allowing a follow-up working. Such specimen piece, obtained by working a large specimen and lifted out therefrom, is not fixed in a lying state on an organic thin film, but a specimen of a thickness of several tens of micrometers, not yet worked to a thin piece, is fixed on a block-shaped sample base in a standing state of a cross-sectional part to be observed, as illustrated in FIG. 3A, and is subjected to finish working on both sides as shown in FIG. 3B.

As in the prior method shown in FIG. 5, an FIB irradiation is executed under blowing of a raw material gas in the vicinity of the upper surface of the cross section to be observed of the specimen block to apply a protective deposition film, and then a thin piece formation is executed by FIB etching from both sides of such cross section to be observed. The basic technical concept of the invention is to execute such thin piece working by acquiring an amount to be scraped in a 1-line FIB scan, then calculating a number of FIB scans required for scraping a thickness to be worked, and automatically executing such work with interim confirmation at a check point. An apparatus to be utilized can basically be a prior FIB apparatus, but an FIB apparatus functioning also as an electron microscope is easier to use. However, a function of measuring the thickness of the worked part from a microscope image and an operating function of calculating a number of working lines by dividing a working thickness with a scraping amount by an FIB scan line. As the scraping amount by an FIB scan line is variable by an FIB setting condition such as a state of an ion beam to be used, an accelerating voltage, a beam current or a scanning speed, and a material constituting the specimen to be worked, a 1-line working is executed on the worked specimen under a determined FIB setting condition at an initial working, and the working is executed under calculation based on a working amount therein. Data in such operation can be utilized in case of preparing plural specimens of a same type, it is convenient, for later working, to store working amounts corresponding to the FIB set conditions for the materials to be worked, as a table in a data base.

Figure 1D:
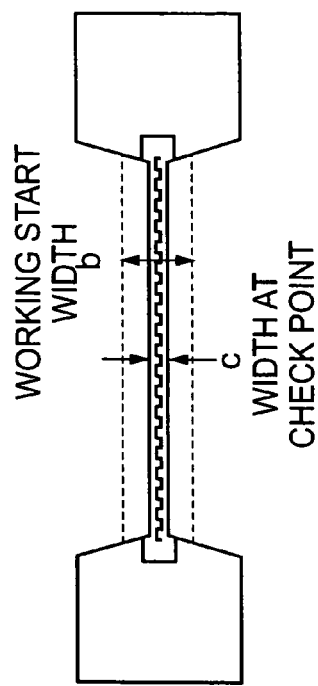
FIGS. 1A–1E are schematic views showing a film thickness control method in the thin film working of the present invention.
Figure 1E:
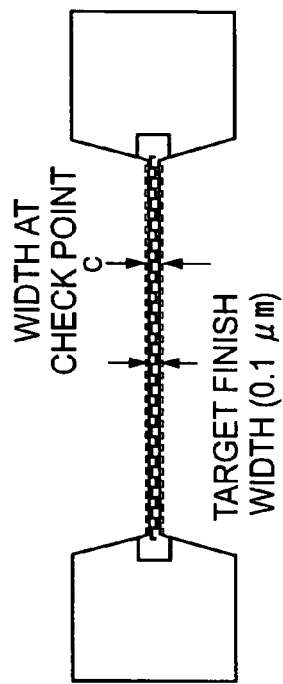
Figure 1A:
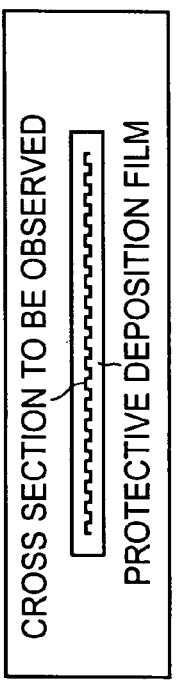
Figure 1B:
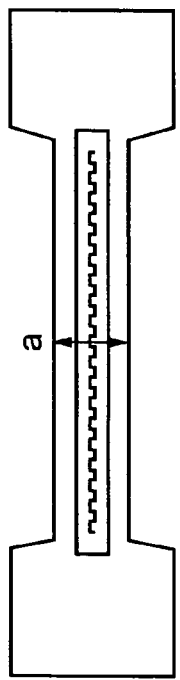
Figure 1C:
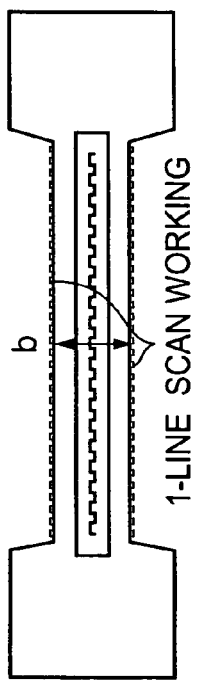

An optimum thickness of a TEM specimen varies depending on a set accelerating voltage of the TEM and the material of the specimen. In general, a material constituted of a heavier element has to be worked thinner as the electrons become less transmittable. As a reference, it is already known that an optimum thickness is about 0.1 $\mu$m in case the specimen is a silicon specimen semiconductor device and the accelerating voltage of TEM is 200 kV. A TEM specimen producing sequence of the invention will be explained with reference to a flow chart shown in FIG. 2. At first, in a step 1, a small piece specimen lifted out from a large specimen such as a wafer is set on a stage of the FIB apparatus, then a microscope image from above is taken to confirm the position of the cross sectional portion to be observed, and an FIB irradiation is executed under blowing the raw material gas to apply a protective deposition film in the vicinity of an upper surface of such cross section to be observed. This state is shown in FIG. 1A. In a step 2, an FIB etching is executed so as to bring the width dimension of the small piece specimen to several times of a target finished width. It is not necessary to obtain an exact dimension in this working, but the final surface has to be finished as a flat surface. Therefore, a rough working is secured at first with a large current, then an intermediate working is executed, and a finish working is executed at a final stage by an FIB of a low current. This state is shown in FIG. 1B. In a step 3, a SIM image is taken, and width dimension a of the specimen is measured by the length-measuring function. In a step 4, conditions are set for an accelerating voltage, a beam current and a scanning speed for the FIB for a fine working, and an etching work of one to several lines is executed. In this operation, working of one to several lines is executed on both sides, so that the working amount substantially corresponds to that for lines of a twice that number (FIG. 1C). In a step 5, a width dimension b after the working is measured by the microscopic length-measuring function, and a dimension scraped by a single scan is obtained from a difference a−b from the former measurement. A step 6 calculates a work amount to a check point. For example, in case the finish width is 0.1 μm and a check point is to be set at a point corresponding to 80% of a range from the current width to the target finish width, the width dimension is given by 0.8(b−0.1) and the number of FIB scans required for working to such point can be given by dividing the aforementioned value with a scraping dimension per a scan, namely:

0.8(b−0.1)/(a−b)/number of working scans.

The FIB etching is executed with a work amount obtained in the step 7. In a step 8, the width dimension c of the worked specimen is measured by the microscopic length-measuring function, and a dimension b−c scraped in the foregoing working is divided by the number n of the actually executing working scans to obtain a more exact working amount per 1-line scan (FIG. 1D). This value, obtained by an average of n-line scans, is more exact than the value (b−a) obtained in 1-line scan in the step 4. This value is employed in case data are stored for preparing specimens of a same type. In a step 9, a width dimension c−0.1 to the target finish dimension is divided by such exact working amount in 1-line scan to calculate a number of working scans to the target finish dimension. In a step 10, a working is executed with the scans of thus calculated number, thus approximately completing the preparation (FIG. 1E). A step 11 confirms the finished state of the specimen, and a fine adjustment is executed if necessary. The confirmation can be executed in a simple manner, in an apparatus provided with TEM means, by obtaining a TEM image therein.

In the foregoing producing sequence, the check point can be selected with suitably selected width and number, and a unit working width in working is preferably selected larger in case the difference to the set value is larger and is made smaller as the set value is approached. Also, as an over scraping cannot be re-worked, the target dimension is preferably set somewhat thicker in consideration of a safety factor.

As to the microscopic length-measuring function, in a system equipped with a monitor SEM, a SEM image or a reflected electron image asynchronous with the FIB can be used as a monitor image. The length-measuring operation can be achieved by executing a pattern matching based on a drift correcting mark provided on a specimen surface, and measuring a remaining width of the designated part of the TEM specimen on real-time basis.

Also in case means are provided for obtaining an image utilizing a signal of electrons reflected or transmitted by the thin film under an electron beam irradiation or X-rays induced by electrons, in the method of estimating the film thickness of the specimen in the course of FIB working, a pattern matching is executed based on a drift correcting pattern, then a position designated for measurement is identified by a pattern matching utilizing a specific pattern of the cross section, and the thickness of the specimen in a finished surface of the TEM specimen is checked by the electron transmission. In this method, it is necessary to measure in advance a relationship between a film thickness of a material same as that of the position designated for measurement and a signal obtained therefrom.

Now there will be explained a system for executing the method of the present invention. In the system of the invention, it is essential to have, as a basic configuration, an ion source such as provided in a prior art FIB apparatus, an ion lens system, a secondary charged particle detector, a gas gun, a monitor for displaying a microscope image, and a controller (computer) for controlling operations and means of condition setting of the FIB, and position control of beam scanning and specimen. In addition, there are required microscopic length-measuring means, memory means and calculation means. The microscopic length-measuring means acquires a microscope image of an upper surface of the specimen and automatically measures the width of the thin film in the steps 3, 5 and 8. The calculation means calculates, in the steps 5, 6, 7 and 8, a difference in the thin film width before and after the working with the FIB of a predetermined condition, a 1-line working amount and a number of line scans required for the working. The memory means stores the specified positional information, the measured width information and the calculated result information in the steps 1, 3, 5, 6, 8 and 9.

Function of each constituent of the present system in each step will be explained according to the flow chart shown in FIG. 2.

Step 1: A small piece specimen is set on the stage of the FIB apparatus, and a microscope image from above is taken to specify the position of the cross-sectional part to be observed. A mark serving as an index for specifying position is given to a specimen surface, then a position of the cross section to be observed is specified on the microscope image based on such point, and the information of such position is stored in the memory means. Based on the positional information, an FIB irradiation is executed under blowing of a raw material gas to form a protective deposition film in the vicinity of the upper surface of the cross section to be observed.

Step 2: When the working is executed on both sides so as to reach several times of a target finished width, since an exact positioning is unnecessary, the etching is executed with an empirical FIB setting according to the material of the specimen. However, since it is necessary to obtain a dimensional difference of the width after a next 1-line scan, the final surface has to be finished as a flat surface. Therefore, a rough working with a high-energy FIB at first, and then an intermediate working are executed with a lowered beam energy in the vicinity of the target position, and a polishing work is executed with a low-energy FIB in a final state. Such operation can be automatically set by a program on the system.

Step 3: A SIM image is obtained, and a width dimension a of the specimen in this state is measured by the length-measuring function.

Step 4: Set conditions on an accelerating voltage, a beam current and a scanning speed of FIB for fine working are determined (usually same as the polishing work in the step 2) and a 1-line etching is executed. This operation is executed by 1 line on each side.

Step 5: A width dimension b after the working is measured by the microscopic length-measuring function, then the calculating means executes a subtraction a−b from the previously measured width to obtain a dimension scraped by a single scan. This data is memorized in the memory means.

Step 6: A work amount to the check point is calculated. For example, in case the finish width is 0.1 μm and a check point is to be set at a point corresponding to 80% of a range from the current width to the target finish width, the width dimension is given by 0.8(b−0.1) and the calculating means calculates a number of FIB scans required for working to such point by "0.8(b−0.1)/(a−b)/number of working scans".

Step 7: The number of the scans for the work amount calculated in the step 6 is set, and the FIB etching is executed.

Step 8: The width dimension c of thus worked specimen is measured by the microscopic length-measuring function. The width dimension c of the specimen in this state need not match strictly with the initially anticipated value. However the width dimension c measured by the microscopic length-measuring function has to be measured exactly. The calculating means calculates a dimension b−c scraped in the foregoing working and divides it with the number n of the actually executing working scans to obtain a working amount per 1-line scan. As explained in the foregoing, this value represents a 1-line working amount which is far exacter than the value "(a−b)/work scan number" obtain only by the 1-line scan in the step 4. This value is stored in the memory means, and can be utilized not only in a next finish working but also in the preparation of specimens of a similar kind.

Step 9: The calculating means calculates a width dimension c−0.1 to the target finish dimension and divides it with such exact working amount in 1-line scan to calculate a number of working scans to the target finish dimension.

Step 10: A working is executed with the scans of thus calculated number, thus approximately completing the preparation. This working, being an automatic working based on the highly precise width dimension c−0.1 and the exact 1-line scan working amount, does not require a particular skill and ensures an extremely precise target finish dimension.

Step 11: The finished state of the prepared specimen is checked, and a fine adjustment is executed if necessary. The confirmation can be executed easily, in an apparatus provided with an electronic microscope apparatus functioning asynchronously with the FIB, by utilizing a SEM image or a reflected electron image as the microscope image. Also in a system including electron beam irradiation means and means for detecting a signal of electrons reflected or transmitted or an of X-rays induced by electrons, the final point of FIB working in the step 10 can be confirmed by monitoring the microscope image based on such detection signal.

The fine working method of the present invention for a TEM specimen etc., including acquiring a work amount in a 1-line scan by an FIB under a predetermined condition, measuring a remaining work width of a thin film on an upper surface of a specimen by a microscopic length-measuring function, determining a required number of scan lines to reach a predetermined width by calculation, and executing a work to obtain a set thickness, can easily execute the production of the TEM specimen even without a trained skill or a recipe for preparation.

The fine working method of the present invention for a TEM specimen etc., capable of obtaining an exact working amount in a 1-line scan by working the specimen in plural line scans with an FIB under a predetermined condition, measuring an etching dimension by a microscopic length-measuring function, and calculating an average working amount in a 1-line scan, can achieve a highly precise TEM specimen working by an automatic working.

The microscopic length measurement in the invention executes a pattern matching based on a drift correcting mark provided on a specimen surface, utilizing a SIM image by the working FIB or a monitoring SEM image, thereby enabling to execute the fine working of the designated position under an exact position matching.

The fine working method of the present invention for a TEM specimen, etc. can ensure precision and stability of the working, as it is executed under confirmation of the thickness of the specimen in a finished surface of the TEM specimen, utilizing a signal of electrons reflected or transmitted by the thin film under an electron beam irradiation or of X-rays induced by electrons.

The system of the present invention for executing fine working for a TEM specimen etc., including means which memorizes a work amount of a line by an FIB under a specified condition, means which acquires a microscope image of an upper surface of the specimen thereby automatically measuring a remaining work width of a thin film, means which calculates a required number of scan lines to reach a predetermined width based on the work amount per line and the remaining work width of the thin film, and means which executes an FIB work, can execute an automatic working to a target thickness, under confirmation of a work amount by measuring the remaining work width of the thin film according to a set program even without a trained skill or a recipe for preparation.

Also the system of the present invention for executing fine working for a TEM specimen etc., including an electron microscope apparatus functioning asynchronously with the FIB, and utilizing a SEM image or a reflected electron image as the microscope image, can execute a pattern matching based on a drift correcting mark provided on a specimen surface, and executes the fine working of the designated position under an exact position matching.

Furthermore, the system of the present invention for executing fine working for a TEM specimen etc., being provided with electron beam irradiating means and means which detects a signal of reflected or transmitted electron or of an electron-induced X-ray, can execute the working under confirmation of the thickness of the specimen by the detection signal and provides precision and stability of the working.

What is claimed is:

1. A thin specimen producing method comprising the steps of:
    acquiring a work amount of a specimen in a one-line scan by a charged particle beam of a charged particle beam apparatus;
    measuring a remaining work width of the specimen by a microscopic length-measuring function of the charged particle beam apparatus;
    determining a required number of scan lines to reach a predetermined width by calculation; and
    executing a work to obtain a set thickness.

2. A thin specimen producing method according to claim 1, wherein the work amount of a specimen in one-line scan is obtained by working the specimen by scanning plural lines of the specimen, measuring a remaining work width of the specimen by a microscopic length-measuring function of the charged particle beam apparatus, and calculating an average work amount per one-line scan.

3. A thin specimen producing method according to claim 1, wherein the microscopic length measurement executes, utilizing a microscope image by the charged particle beam or a monitoring microscope image, a pattern matching based on a drift correcting mark provided on a specimen surface, thereby measuring a specimen thickness of a finished surface in a designated part of the thin specimen.

4. A thin specimen producing method according to claim 1, wherein a specimen thickness of a finished surface of the thin specimen is confirmed by a signal of electrons reflected or transmitted by a thin film under an electron beam irradiation, or of electron-induced X-rays.

5. A thin specimen producing apparatus comprising:
   means for memorizing a thinning amount of a specimen in a one-line scan by a charged particle beam apparatus;
   means for acquiring a microscope image of an upper surface of the specimen thereby automatically measuring a remaining width of the specimen in a thinning process;
   means for calculating a required number of scan lines to reach a predetermined width based on the thinning amount per line and the remaining width of the specimen; and
   means for executing the required number of scans by the charged particle beam apparatus.

6. A thin specimen producing apparatus according to claim 5, further comprising an electron microscope apparatus functioning asynchronously with the charged particle beam apparatus, wherein a SEM image or a reflected electron image is sued as the microscope image.

7. A thin specimen producing apparatus according to claim 5, further comprising electron beam irradiating means and means for detecting a signal of reflected or transmitted electrons or of electron-induced X-rays, the working thickness being confirmed by the detection signal.

* * * * *